US006140298A

United States Patent [19]

Racherla et al.

[11] Patent Number: 6,140,298

[45] Date of Patent: Oct. 31, 2000

[54] BLEACHING COMPOSITIONS BASED ON AIR, UNCOMPLEXED TRANSITION METAL IONS AND AROMATIC ALDEHYDES

[75] Inventors: Uday Shanker Racherla, West Caldwell; Robert Charles Vermeer, Nutley, both of N.J.

[73] Assignee: Lever Brothers Company, division of Conopco, Inc., New York, N.Y.

[21] Appl. No.: 09/212,620

[22] Filed: Dec. 16, 1998

[51] Int. Cl.[7] .......... C11D 3/00; C11D 3/395; D06L 3/00

[52] U.S. Cl. .......... 510/367; 510/302; 8/111

[58] Field of Search .......... 510/367, 302; 8/111

[56] References Cited

U.S. PATENT DOCUMENTS

| | | | |
|---|---|---|---|
| 1,163,438 | 12/1915 | Muller . | |
| 3,502,715 | 3/1970 | Inoue et al. | 260/502 |
| 3,822,114 | 7/1974 | Montgomery . | |
| 4,006,092 | 2/1977 | Jones . | |
| 4,434,086 | 2/1984 | Hill et al. . | |
| 4,476,041 | 10/1984 | Hill et al. . | |
| 4,784,790 | 11/1988 | Disch et al. . | |
| 5,234,832 | 8/1993 | Disch et al. . | |
| 5,527,769 | 6/1996 | Winter et al. . | |
| 5,552,379 | 9/1996 | Winter et al. . | |
| 5,882,355 | 3/1999 | Koek | 8/111 |

FOREIGN PATENT DOCUMENTS

| | | |
|---|---|---|
| 993 755 | 7/1976 | Canada . |
| 0 050 015 | 4/1982 | European Pat. Off. . |
| 0 125 103 | 11/1984 | European Pat. Off. . |
| 0 653 420 | 5/1995 | European Pat. Off. . |
| 2148302 | 3/1973 | France . |
| 63-92698 | of 1988 | Japan . |
| 01117859 | 5/1989 | Japan . |
| 98/06813 | 2/1988 | WIPO . |
| 97/34986 | 9/1997 | WIPO . |
| 97/38074 | 10/1997 | WIPO . |

OTHER PUBLICATIONS

Kiyotomi Kaneda et al, J. Chem. Soc., Chem. Commun., 1990, 1467–1468.

Shun–Ichi Murahashi et al., J. Am. Chem. Soc. 1992, 114, 7913–7914.

Teruaki Mukaiyama et al, Bull. Chem. Soc. Jpn., 68, 17–35 (1995).

*Primary Examiner*—Yogendra Gupta
*Assistant Examiner*—John M. Petruncio
*Attorney, Agent, or Firm*—Milton L. Honig

[57] ABSTRACT

A bleach composition and a method for bleaching stains is provided, the composition including a $C_7$–$C_{20}$ aromatic aldehyde and a transition metal salt. Air is employed as source of oxygen which combines with the aldehyde to form the bleach active species. Peroxides, inorganic persalts and bleach precursors are unnecessary elements for the bleach systems of this invention.

13 Claims, No Drawings

BLEACHING COMPOSITIONS BASED ON AIR, UNCOMPLEXED TRANSITION METAL IONS AND AROMATIC ALDEHYDES

BACKGROUND OF THE INVENTION

1. Field of the Invention

The invention concerns compositions and processes for bleaching substrates directly with air.

2. The Related Art

Oxygen bleaches are well known for their ability to remove stains from substrates. Traditionally the substrate is subjected to hydrogen peroxide or substances which can generate hydroperoxyl radicals. The latter may be inorganic or organic peroxides. Generally these systems must be activated. A method of activation is to employ wash temperatures of 60° C. or higher. Unfortunately, these high temperatures often lead to inefficient cleaning. They can also cause premature damage to the substrate.

A preferred approach to generating hydroperoxyl bleach radicals is the use of inorganic peroxides coupled with organic precursor compounds. These systems are employed for many commercial laundry powders. European systems are based on tetraacetyl ethylenediamine (TAED) as the organic precursor coupled with sodium perborate or sodium percarbonate. Well known in the United States are laundry bleach products based on sodium nanonyloxybenzenesulphonate (SNOBS) as the organic precursor coupled with sodium perborate. Precursor systems are generally effective yet they still exhibit several disadvantages. For example, organic precursors are moderately sophisticated molecules requiring multi-step manufacturing processes resulting in high capital costs. Secondly, precursor systems have large formulation space requirements; a significant percent of a laundry powder must be devoted to the bleach components leaving less room for other active ingredients and complicating development of concentrated powders. Moreover, precursor systems do not bleach very efficiently in countries where consumers have wash habits entailing low dosage, short wash times, cold temperatures and low wash liquor to cloth ratios.

A long cherished dream has been to use air directly as the oxygen source. Air would avoid costly synthesized organic precursors. Unfortunately, air is kinetically inert towards bleaching substrates due to the spin barrier restriction and exhibits no bleaching ability. Recently some progress has been made in this area.

WO 97/38074 reports use of molecular oxygen (air) for oxidizing stain from fabrics. It was discovered that fabrics can be bleached by bubbling air through an aqueous solution containing an aldehyde. A broad range of aliphatic, aromatic and heterocyclic aldehydes were reported to be useful, particularly para-substituted aldehydes such as 4-methyl-, 4-ethyl- and 4-isopropyl benzaldehyde. It was also necessary in these systems to employ a radical initiator. A broad range of initiators were disclosed including N-hydroxysuccinimide, various peroxides and transition metal coordination complexes. Moreover, the pH range of operability was broadly disclosed as being from 4 to 12, but preferably in the range of 7 to 10 with most experiments being performed at pH 7. While this disclosure appears to be a step-change in bleach chemistry, it is clear that more work is required to reveal the optimum system.

Accordingly, it is an object of the present invention to provide an optimum bleaching system with improved stain removal efficacy based on air or molecular oxygen.

Another object of the present invention is to provide a bleaching system which is cost-effective and environmentally friendly.

Still another object of the present invention is to provide a bleaching system based on air this is operable under harsh water conditions which includes relatively low temperatures, short contact times and low dosage requirements.

Yet another object of the present invention is to provide an improved hygiene or antimicrobial benefit coupled with a reduction in dye transfer.

These and other objects of the present invention will become more readily apparent from the following summary and detailed description.

SUMMARY OF THE INVENTION

A bleaching composition is provided which includes:

(i) an effective amount for stain removal of a $C_7$–$C_{20}$ aromatic aldehyde;

(ii) air as a primary source of oxygen atoms to combine with the aldehyde; and (iii) an effective amount to activate the aldehyde of an uncomplexed transition metal salt.

Furthermore, a method for bleaching stains from substrates is provided by treating the substrates with air (molecular oxygen), an aromatic aldehyde and an uncomplexed transition metal salt in an aqueous medium.

DETAILED DESCRIPTION OF THE INVENTION

Now it has been discovered that stains can be removed simply by air oxidation through the intermediacy of a $C_7$–$C_{20}$ aromatic aldehyde in conjunction with uncomplexed transition metal salts. Each of these elements will be described in more detail below.

An essential feature of the present invention is a $C_7$–$C_{20}$ aromatic aldehyde. Particularly advantageous are aromatic aldehydes selected from those having a calculated logP ranging from about 2 to about 3. The term logP is the mathematical log value of the partition coefficient for solubility of the aldehyde between water and 1-octanol. It is a property of a two-phase system in which 1-octanol and water are in equilibrium, at a fixed temperature, and an organic substance is distributed between these phases. LogP is best defined as the equilibrium distribution or the ratio of an organic substance in the 1-octanol phase to that in the water phase. In general, logP tends to be small for polar hydrophilic substances and large for nonpolar hydrophobic substances. Thus logP provides a measure of the hydrophilic vs. hydrophobic nature (HLB balance) of a compound, which is an important consideration in assessing solubility. We have found that aldehydes outside the calculated logP range of about 2 to 3 do not bleach and are ineffective. Even more advantageous are aromatic aldehydes that are liquids and have a total carbon content from 7 to 15, preferably from 7 to 10, and optimally from 8 to 9 carbon atoms. Examples, of specific aromatic aldehydes which are particularly effective include: 2-methylbenzaldehyde, 3-methylbenzaldehyde, 4-methylbenzaldehyde, 2-chlorobenzaldehyde, 2,3-dimethylbenzaldehyde, 2,4-dimethylbenzaldehyde, 2,5-dimethylbenzaldehyde, 3,6-dimethylbenzaldehyde, 3,4-dimethylbenzaldehyde, 3,5-dimethylbenzaldehyde, 4,5-dimethylbenzaldehyde, 4,6-dimethylbenzaldehyde, 5,6-dimethylbenzaldehyde, 2-ethylbenzaldehyde, 2-trifluoromethylbenzaldehyde, 4-ethylbenzaldehyde, 3-ethylbenzaldehyde, 2,3,4-trimethylbenzaldehyde, 2,3,5-trimethylbenzaldehyde, 2,3,6-trimethylbenzaldehyde, 2,4,5-trimethylbenzaldehyde, 2,4,6-trimethylbenzaldehyde, 2,5,6-trimethylbenzaldehyde, 3,4,5-trimethylbenzaldehyde, 3,4,6-trimethylbenzaldehyde, 3,5,6-trimethylbenzaldehyde, 4,5,6-trimethylbenzaldehyde and the like.

For purposes of this invention it is to be understood that the term aromatic aldehyde encompasses substituted aromatic rings. Illustrative but not limiting examples of substituted groups are alkyl (particularly methyl and ethyl), trifluoromethyl, carboxy, phospho, sulpho, chloro, bromo, fluoro, cyano, alkoxy, nitro, amino, quaternary ammonium, hydroxyalkyl and combinations thereof. Of course, the choice of substituent must allow the aldehyde to fall within the acceptable calculated logP value of about 2 to about 3 and other criteria previously specified for optimum bleaching performance.

Amounts of the aromatic aldehyde may range from about 0.01 to about 80%, preferably from about 0.1 to about 50%, more preferably from about 0.5 to about 20%, optimally from about 1 to about 5% by weight of the bleaching composition.

A second essential element of the present invention is that of an uncomplexed transition metal salt. By the term "uncomplexed" is meant any simple salt of a transition metal which does not include covalent bonded ligands to the transition metal atoms. Particularly excluded are nitrogen based ligands, most especially ligands such as 1,4,7-trimethyl-1,4,7-triazacyclononane and N,N-bis(pyridin-2-yl-methyl)-bis (pyridin-2-yl)-methylamine.

Transition metals encompassed within this invention are manganese, iron, cobalt, molybdenum, tungsten, copper, chromium, nickel, palladium, platinum, rhodium and combinations thereof. These transition metals may form a salt with inorganic or organic ions. Illustrative inorganic ions may be those selected from the group consisting of fluoride, chloride, bromide, iodide, nitrate, nitrite, perchlorate, sulphate, phosphate, hydroxide, oxide, hydroperoxide, sulfide, azide, thiocyanate, isothiocyanate, borate, carbonate, silicate and combinations thereof. Illustrative organic ions may be $C_1$–$C_{20}$ moieties selected from the group consisting of acetate, lactate, propionate, benzoate, methosulphate, toluenesulphonate, p-nitrobenzenesulphonate, formate and combinations thereof.

Amounts of the transition metal salt may range from about 0.01 ppm to about 10%, preferably from about 0.1 ppm to about 5%, more preferably from about 1 ppm to about 50 ppm by weight of the bleaching composition. The weight ratio of aldehyde to transition metal salt may range from about $1\times10^9$:1 to about 1:2, preferably from about $3\times10^6$:1 to about 1:1. Most preferred among the transition metals are cobalt and iron as well as mixtures thereof.

Optionally the compositions of this invention may also include other promoters. Among the most preferred are the aromatic imides of the general structure:

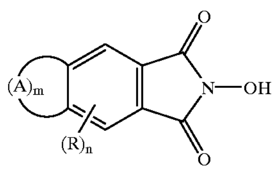

wherein

A is $CX_q$ and X is selected from the group consisting of hydrogen, $C_1$–$C_5$ alkyl, a heteroatom substituent and mixtures thereof, where q is independently 1 or 2;

R is a moiety, which when hydrocarbyl may have from 1 to 7 carbon atoms, and is selected from the group consisting of hydrogen, alkyl, cycloalkyl, aryl, alkoxy, hydroxy, acyloxy, halo, carboxy, amino, quaternary amino, sulpho, phospho, cyano radicals and mixtures thereof;

m and n may independently range from 0 to 4.

Particularly preferred substituents are methyl, ethyl, isopropyl, chloro, trifluoromethyl, methoxy, acetyl and cyclic groups such as pyridyl, naphthyl, phenyl, furanyl and indolyl radicals. Most preferred is the unsubstituted generic structure where m and n are both 0; this material is known as N-hydroxyphthalimide (NHPI). Examples of other potentially useful structures are outlined below.

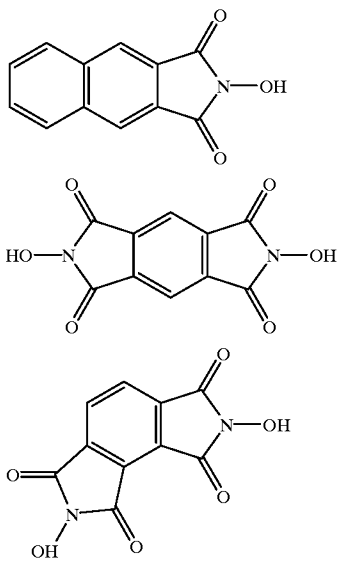

Amounts of the imide may range from about 0.001 to about 65%, preferably from about 0.01 to about 7%, more preferably from about 0.01 to about 1% by weight of the bleaching composition. The weight ratio of aldehyde to imide may range from about 500:1 to about 1:2, preferably from about 100:1 to about 1:1.

Bleach systems of the present invention may be employed for a wide variety of purposes. These include cleaning hard surfaces, food utensils, kitchenware, floors, bathtubs, hair, carpets, dentures and fabrics. Most especially the systems are useful in the cleaning of laundry and kitchenware. When intended for such purpose, the aldehyde and imide of the present invention may usually be combined with surface-active materials, detergency builders and other known ingredients of detergent formulations.

The surface-active material (i.e. surfactants or cleansing agents) may be naturally derived, or synthetic material selected from anionic, nonionic, amphoteric, zwitterionic, cationic actives and mixtures thereof. Many suitable actives are commercially available and are fully described in the literature, for example in "Surface Active Agents and Detergents", Volumes I and II, by Schwartz, Perry and Berch. The total level of the surface-active material may range up to 50% by weight, preferably being from 0.5 to 40% by weight of the composition, most preferably 4 to 25%.

Synthetic anionic surface-actives are usually water-soluble alkali metal salts of organic sulphates and sulphonates having alkyl radicals containing from about 8 to about 22 carbon atoms.

Examples of suitable synthetic anionic detergent compounds are sodium and ammonium alkyl sulphates, especially those obtained by sulphating higher ($C_8$–$C_{18}$) alcohols produced for example from tallow or coconut oil; sodium and ammonium alkyl ($C_8$–$C_{20}$) benzene sulphonates, sodium alkyl glyceryl ether sulphates, especially those ethers of the higher alcohols derived from tallow or coconut oil and synthetic alcohols derived from petroleum; sodium coconut oil fatty acid monoglyceride sulphates and sulphonates; sodium and ammonium salts of sulphuric acid esters of higher ($C_9$–$C_{18}$) fatty alcohol-alkylene oxide, particularly ethylene oxide, reaction products; the reaction products of fatty acids such as coconut fatty acids esterified with isethionic acid and neutralized with sodium hydroxide; sodium and ammonium salts of fatty acid amides of methyl taurine; sarcosinate salts; alkane monosulphonates such as those derived by reacting alpha-olefins ($C_8$–$C_{20}$) with sodium bisulphite and those derived by reacting paraffins with $SO_2$ and $Cl_2$ and then hydrolyzing with a base to produce a random sulphonate; sodium and ammonium $C_7$–C12 dialkyl sulfosuccinates; and olefin sulphonates, which term is used to describe the material made by reacting olefins, particularly $C_{10}$–$C_{20}$ alpha-olefins, with $SO_3$ and then neutralizing and hydrolyzing the reaction product, sulphated or sulphonated alkyl polyglucosides, sulphated alkyl methyl glucamides, sulphated lactobionamides and combinations thereof. The preferred anionic detergent compounds are sodium ($C_{11}$–$C_{15}$) alkylbenzene sulphonates, sodium ($C_{16}$–$C_{18}$) alkyl sulphates and sodium ($C_{16}$–$C_{18}$) alkyl ether sulphates.

Examples of suitable nonionic surface-active compounds which may be used, preferably together with the anionic surface-active compounds, include in particular the reaction products of alkylene oxides, usually ethylene oxide, with alkyl ($C_6$–$C_{22}$) phenols, generally 5–25 EO, i.e. 5–25 units of ethylene oxide per molecule; the condensation products of aliphatic ($C_8$–$C_{18}$) primary or secondary linear or branched alcohols with ethylene oxide, generally 2–30 EO, and products made by condensation of ethylene oxide with the reaction products of propylene oxide and ethylene diamine. Other so-called nonionic surface-actives include alkyl polyglucosides, long chain tertiary amine oxides, and fatty amido polyols such as alkyl methyl glucamides and alkyl lactobionamides.

Amphoteric or zwitterionic surface-active compounds such as alkylamidopropyl betaines can also be used in the compositions of the invention. If any amphoteric or zwitterionic detergent compounds are used, it is generally in small amounts in compositions based on the much more commonly used synthetic anionic and nonionic actives.

Soaps may also be incorporated into the compositions of the invention, preferably at a level of less than 30% by weight. They are particularly useful at low levels in binary (soap/anionic) or ternary mixtures together with nonionic or mixed synthetic anionic and nonionic compounds. Soaps which are used are preferably the sodium, or less desirably potassium, salts of saturated or unsaturated $C_{10}$–$C_{24}$ fatty acids or mixtures thereof. The amount of such soaps can be varied between 0.5 and 25% by weight, with lower amounts of 0.5 to 5% being generally sufficient for lather control. Amounts of soap between 2 and 20%, especially between 5 and 15, are used to give a beneficial effect on detergency. This is particularly valuable in compositions used in hard water where the soap acts as a supplementary builder.

In systems where anionic surfactants such as linear alkylbenzene sulphonate are employed, it may be desirable to include a hydrotrope or phase regulant such as alkali metal benzene sulphonate, toluene sulphonate and ethyl benzene sulphonate thereby improving the bleaching effect.

The detergent compositions of the invention will normally also contain a detergency builder. Builder materials may be selected from (1) calcium sequestrant materials, (2) precipitating materials, (3) calcium ion-exchange materials and (4) mixtures thereof.

In particular, the compositions of the invention may contain any one of the organic or inorganic builder materials, such as sodium, potassium, lithium or magnesium salts of tripolyphosphate, pyrophosphate, orthophosphate, carbonate, nitrilotriacetic acid, citrate, carboxymethylmalonate, carboxymethyloxysuccinate, tartrate mono- and di- succinate, oxydisuccinate, bicarbonate, tetraborate, tetraboratedecahydrate, crystalline or amorphous aluminosilicates and mixtures thereof. Most preferred among the builders are the salts of carbonate, sesquicarbonate, bicarbonate and borate as well as zeolite and mixtures thereof.

Polycarboxylic homo- and co-polymers may also be included as builders and to function as powder structurants or processing aids. Particularly preferred are polyacrylic acid (available under the trademark Acrysol from the Rohm and Haas Company) and acrylic-maleic acid copolymers (available under the trademark Sokalan from the BASF Corporation) and alkali metal or other salts thereof.

These builder materials may be present at a level of from about 1 to 80% by weight, preferably from about 10 to 60% by weight.

Upon dispersal in a wash water, the initial amount of aldehyde should range anywhere from about 0.1 to about 30 mmol/liter, preferably from about 1 to about 15 mmol/liter of the aqueous wash liquor. The N-hydroxy imide can range anywhere from about 0.001 to about 10 mmol/liter, preferably from about 0.01 to about 2 mmol/liter. Surfactant when present in the wash water may range from about 0.05 to about 1.0 grams/liter, preferably from about 0.15 to about 0.25 grams/liter. When present, the builder amount may range from about 0.1 to about 3.0 grams/liter.

Often the aldehydes of the present invention are sensitive to certain detergent ingredients as well as to air; they can be protected by encapsulation or some other suitable protective barrier. Methods of encapsulation are described in U.S. Pat. No. 5,385,959, U.S. Pat. No. 5,441,660 and U.S. Pat. No. 5,434,069. Examples of preferred encapsulation polymers include, but are not limited to, polyvinyl alcohol, polyacrylamide, polyvinyl pyrrolidone, carrageenan, guar gum, xanthan gum and celluloses.

Apart from the components already mentioned, the bleaching compositions of the invention may contain any of the conventional additives in the amounts in which such materials are normally employed in cleaning compositions. Examples of these additives include dye transfer inhibition agents such as polyamine N-oxide polymers, metallo phthalocyanines, and polymers based on N-vinylpyrrolidone and N-vinylimidazole, lather boosters such as alkanolamides, particularly the monoethanolamides derived from palmkernel fatty acids and coconut fatty acids, lather-depressants such as alkyl phosphates and silicones, anti-redeposition agents such as sodium carboxymethylcellulose and alkyl or substituted alkylcellulose ethers, stabilizers such as ethylene diamine tetraacetic acid and phosphonic acid derivatives (Dequest®), fabric softening agents, inorganic salts such as sodium sulphate, and, usually present in very small amounts, fluorescent agents, perfumes, enzymes such as proteases, cellulases, lipases and amylases, germicides and colorants.

The aldehydes in combination with the imide may be useful for removing stains both in consumer type products and for industrial applications. Among consumer products incorporating this invention are laundry detergents, laundry bleaches, hard surface cleaners, toilet bowl cleaners, automatic dishwashing compositions and even denture cleansers. Stained consumer products benefiting from treatment with compositions of this invention may include clothes and other fabrics; household fixtures and appliances such as sinks, toilet bowls and oven ranges; tableware such as drinking glasses, dishes, cookware and utensils; and dentures. Hair colorants may also be formulated with the bleach composition of this invention. The bleaching system of this invention may also be applied to industrial uses such as for the bleaching of wood pulp.

The system of the present invention may be delivered in a variety of product forms including powders, on sheets or other substrates, in pouches, in tablets, in aqueous liquids, or in nonaqueous liquids such as liquid nonionic detergents, aerosol, gel, cream or granular form.

The following examples will more fully illustrate the embodiments of this invention. All parts, percentages and proportions referred to herein and in the appended claims are by weight unless otherwise specified.

EXAMPLE 1

A general outline of the essential steps in our experimental protocol are shown below.

An Outline of the Essential Protocol Steps a) Measure the initial reflectance of the swatches ($R_i$).

b) Saturate the wash solution with air.

c) Wash, rinse and dry the swatches.

d) Measure the final reflectance of the swatches ($R_f$).

All work was conducted in a Tergotometer with 2L stainless steel pots. The swatches were dried flat on a rack in a Kenmore dryer. Each experiment was performed once with 2 replicate pots containing the same aldehyde (average of 2 values), except for the exceptional bleaching aldehydes, which were repeated 3 times with 2 replicate pots containing the same aldehyde (average of 6 values). The conditions utilized were as follows:

| Conditions for Saturating the Wash Solution with Air | |
|---|---|
| Saturation Time | 15 mins |
| Agitation | 100 rpm |
| Water Volume | 1 L |
| Hardness | None |
| Air Rate | 532 ml/min. |
| Temperature | 25° C. |

-continued

| Wash Conditions | |
|---|---|
| Wash Time | 30 mins |
| Agitation | 100 rpm |
| Water Volume | 1 L |
| Hardness | None |
| Buffer | Carbonate |
| pH | 8 or 10 |
| Air Rate | 532 ml/min |
| Temperature | 25° C. |
| Test cloths | Tea (BC-1) |
| Ballast | None |
| L/C Ratio | 208:1 |
| **Rinse Conditions** | |
| Rinse Time | 3 mins |
| Agitation | 100 rpm |
| Water Volume | 1 L |
| Hardness | None |
| Temperature | 25° C. |
| Replicate Rinses | 2 |

Each Tergotometer Pot was filled with 1 liter of milli-Q-water containing carbonate buffer solution which was saturated for 15 minutes with air under agitation at 25° C. Tea stained (BC-1) swatches were washed for 30 minutes in the presence of aldehyde and air at pH=8 (25° C). The corresponding controls (buffer alone) were performed simultaneously. All swatches were rinsed twice for 3 minutes with agitation at 25° C. and dried flat on a rack in a Kenmore with soft heat for 30 minutes.

Bleaching Evaluation

To quantify the degree of stain removal, the reflectance of 4 stained swatches (4 per pot) were measured before and after washing using a Gardner reflectometer (Model #2000) set at 460*nm (*UV filter). The change in reflectance ($\Delta R$) was determined by taking the difference of the swatch before and after each washing. The standard deviation ($\sigma$) and $\Delta\Delta R_{ave}$ was assigned to each experimental group.

$$\Delta R = R_f - R_i$$

$R_i$=Initial reflectance of stained swatch before washing.
$R_f$=Final reflectance of stained swatch after washing.

$$\Delta R_{aldehyde\ system+control} - \Delta R_{control} = \Delta\Delta R — 1\text{–}3\times — \Delta\Delta R_{ave}$$

$\Delta\Delta R_{ave}$=Represents the average bleaching by the aldehyde system.

EXAMPLE 1

TABLE I

Bleaching Tea Stain By Air and 4-Ethylbenzaldehyde With A Mixture of Metal Ions

| BLEACH SYSTEM | $\Delta\Delta R_{ave}$ |
|---|---|
| 4-EBA + [$Zn^{+2}$, $Fe^{+3}$, $Cu^{+2}$, $Mn^{+2}$; 0.12 ppm] | 1.0 |
| 4-EBA + [$Zn^{+2}$, $Fe^{+3}$, $Cu^{+2}$, $Mn^{+2}$; 0.3 ppm] | 1.7 |
| 4-EBA + [$Zn^{+2}$, $Fe^{+3}$, $Cu^{+2}$, $Mn^{+2}$; 0.6 ppm] | 7.5 |
| 4-EBA + [$Zn^{+2}$, $Fe^{+3}$, $Cu^{+2}$, $Mn^{+2}$; 1 ppm] | 7.4 |
| 4-EBA + [$Zn^{+2}$, $Fe^{+3}$, $Cu^{+2}$, $Mn^{+2}$; 2.8 ppm] | 8.6 |
| 4-EBA + [$Zn^{+2}$, $Fe^{+3}$, $Cu^{+2}$, $Mn^{+2}$; 5.5 ppm] | 9.4 |

*pH = 8; 25° C., 30 minutes wash 20 mM carbonate buffer 15 mM 4-EBA

Table I demonstrates that 0.6 ppm or more of mixtures of metal ions combined with 4-ethylbenzaldehyde produces an exceptional bleaching system.

EXAMPLE 2

TABLE II

Bleaching Tea Stain By Air and 4-Ethylbenzaldehyde With Individual Metal Ions

| BLEACH SYSTEM | $\Delta\Delta R_{ave}$ |
|---|---|
| 4-EBA + Cu (I) Cl | 0.3 |
| 4-EBA + Cu (II) $Cl_2$ | 0.5 |
| 4-EBA + Mo (V) $Cl_5$ | 1.2 |
| 4-EBA + $Na_2$ $WO_4$ | 1.6 |
| 4-EBA + Ca (II) $Cl_2$ | 1.7 |
| 4-EBA + Zn (II) $Cl_2$ | 1.4 |
| 4-EBA + Mo (III) $Cl_3$ | 1.8 |
| 4-EBA + Fe (II) $SO_4$ | 2.1 |
| 4-EBA + Ti (N) $O_2$ | 2.9 |
| 4-EBA + Mn (III) $(OAc)_3$ | 3.0 |
| 4-EBA + Mo (II) $(OAc)_2$ | 3.5 |
| 4-EBA + $Fe_2$ (III) $(SO_4)_3$ | 4.8 |
| 4-EBA + Mn (II) $(AC)_2$ | 6.6 |
| 4-EBA + V (II) O $SO_4$ | 7.6 |
| 4-EBA + Mg (II) $Cl_2$ | 7.8 |
| 4-EBA + Ti (II) O | 7.9 |
| 4-EBA + Mo (VI) $O_3$ | 8.3 |
| 4-EBA + Co (II) $(Ac\ Ac)_2$ | 13.1 |
| 4-EBA + Co (II) $(OAc)_2$ | 14.8 |

*pH = 8; 25° C. 30 minutes wash 20 mM carbonate buffer; 1 ppm 15 mM 4-EBA

Table II suggests that $Fe^{+3}$, $Mn^{+2}$, $V^{+2}$, $Ti^{+2}$, $MO^{+6}$ or $Co^{+2}$ combined with 4-ethylbenzaldehyde produce exceptional bleaching results.

EXAMPLE 3

TABLE III

Bleaching Tea Stain by Air and 4-Ethylbenzaldehyde with Individual Metal Ions

| BLEACH SYSTEM | $\Delta\Delta R_{ave}$ |
|---|---|
| 4-EBA + Ru (III) $(AcAc)_3$ | 0.6 |
| 4-EBA + Ca (II) $Cl_2$ | 1.7 |
| 4-EBA + Fe (II) Phthalocyanine | 6.6 |
| 4-EBA + Mn (II) $(AcAc)_2$ | 5.0 |
| 4-EBA + Mn (III) $(AcAc)_3$ | 6.4 |
| 4-EBA + Co (II) Phthalocyanine | 8.9 |
| 4-EBA + U (III) $(AcAc)_3$ | 6.6 |
| 4-EBA + Fe (III) $(AcAc)_3$ | 9.1 |
| 4-EBA + Co (II) BzAc | 13.1 |
| 4-EBA + Mg $Cl_2$ | 7.8 |
| 4-EBA + Co (II) $(AcAc)_2$ | 13.1 |
| 4-EBA + Co (II) $(NHPI)_3$ Na | 15.7 |
| 4-EBA + Co (III) $(NO_2)_6$ $Na_3$ | 14.6 |
| 4-EBA + Co (II) $(AcAc)_2.2H_2O$ | 16.1 |
| 4-EBA + Co (II) $(NO_3)_2$ | 16.6 |
| 4-EBA + Co (II) $(OAc)_2$ | 17.0 |

*pH = 8; 25° C.; 30 minutes wash; 20 mM carbonate buffer 1 ppm metal ion 15 mM 4-EBA Table III demonstrates that $Fe^{+2}$, $Mn^{+2}$, $Mn^{+3}$, $V^{+3}$, $Fe^{+3}$ or $Co^{+2}$ combined with 4-ethylbenzaldehyde produce exceptional bleaching results.

EXAMPLE 4

TABLE IV

Bleaching Tea Stain By Air and 4-Ethylbenzaldehyde with Individual Metal Ions in The Presence of LAS Surfactant

| BLEACH SYSTEM | $\Delta\Delta R_{ave}$ |
|---|---|
| 4-EBA + Lu (III) $(AcAc)_3$ + LAS | 1.4 |
| 4-EBA + Ca (II) $Cl_2$ + LAS | 2.2 |
| 4-EBA + Fe (II) Phthalocyanine + LAS | 4.9 |
| 4-EBA + Mn (II) $(AcAc)_2$ | 6.5 |
| 4-EBA + Mn (III) $(AcAc)_3$ | 7.2 |
| 4-EBA + Co (II) Phthalocyanine + LAS | 7.4 |
| 4-EBA + U (III) $(AcAc)_3$ + LAS | 7.9 |
| 4-EBA + Fe (III) $(AcAc)_3$ | 10.6 |
| 4-EBA + Co (II) BzAc + LAS | 10.6 |
| 4-EBA + Mg $Cl_2$ + LAS | 12.1 |
| 4-EBA + Co (II) $(AcAc)_2$ + LAS | 13.4 |
| 4-EBA + Co (II) $(NHPI)_3$ Na + LAS | 14.3 |
| 4-EBA + Co (III) $(NO_2)_6$ $Na_3$ + LAS | 14.8 |
| 4-EBA + Co (II) $(AcAc)_2.2H_2O$ + LAS | 15.2 |
| 4-EBA + Co (II) $(NO_3)_2$ + LAS | 16.3 |
| 4-EBA + Co (II) $(OAc)_2$ + LAS | 17.9 |

*pH = 8; 25° C.; 30 minutes wash; 20 mM carbonate buffer; 1 ppm metal ion; 22% LAS; 15 mM 4-EBA Table IV demonstrates that even in the presence of LAS surfactant ions, the $Fe^{+2}$, $Mn^{+2}$, $Mn^{+3}$, $V^{+3}$, $Fe^{+3}$ or $Co^{+2}$ ions combined with 4-ethylbenzaldehyde produce an exceptional bleaching result.

EXAMPLE 5

TABLE V

Bleaching Tea Stain By Air and 4-Ethylbenzaldehyde With Cobalt (II) Acetylacetonate in the Presence of LAS and Zeolite

| BLEACH SYSTEM | $\Delta\Delta R_{ave}$ |
|---|---|
| 4-EBA + Co (II) AcAc + LAS | 13.4 |
| 4-EBA + Co (II) AcAc + Zeolite | 13.0 |
| 4-EBA + Co (II) AcAc + LAS + Zeolite | 14.1 |

*pH = 8; 25° C.; 30 minute wash; 20 mM carbonate buffer; 1 ppm metal ion; 22% LAS; 13.6% zeolite; 45 mM 4-EBA Table V demonstrates that exceptional bleaching benefits are obtained on tea stain with 4-EBA and Co (II) AcAc even in the presence of LAS and Zeolite.

EXAMPLE 6

TABLE VI

Bleaching Tea Stain By Air and 4-Ethylbenzaldehyde With Cobalt Acetate in the Presence of Detergent

| BLEACH SYSTEM | $\Delta\Delta R_{ave}$ |
|---|---|
| 4-EBA + 1 ppm $Co^{+2}$ | 4.7 |
| 4-EBA + 1.3 ppm $Co^{+2}$ | 6.4 |
| 4-EBA + 1.5 ppm $Co^{+2}$ | 8.0 |
| 4-EBA + 2 ppm $Co^{+2}$ | 8.2 |
| 4-EBA + 2.3 ppm $Co^{+2}$ | 8.3 |
| 4-EBA + 2.5 ppm $Co^{+2}$ | 9.4 |
| 4-EBA + 3 ppm $Co^{+2}$ | 12.5 |
| 4-EBA + 5 ppm $Co^{+2}$ | 14.0 |
| 4-EBA + 7 ppm $Co^{+2}$ | 13.8 |
| 4-EBA + 10 ppm $Co^{+2}$ | 14.0 |

*pH = 8; 25° C.; 30 minute wash; 20 mM carbonate buffer; 2.1 g/l detergent base; 15 mM 4-EBA Table VI demonstrates that exceptional bleaching benefits are obtained with $Co^{+2}$ and 4-EBA even in the presence of detergent.

EXAMPLE 7

This Example investigates the effectiveness of cobalt. Table VII illustrates the bleaching effect against tea stains (BC-1) of 4-methylbenzaldehyde in combination with cobalt acetate at various transition metal concentration levels.

TABLE VII

| BLEACH SYSTEM | $\Delta\Delta R_{ave}$ |
|---|---|
| Bleaching Tea Stains by Air and 4-Methylbenzaldehyde With Cobalt Acetate | |
| 4-MBA (15 mM) + 1 ppm Co (II) | 7.8 |
| 4-MBA (15 mM) + 2 ppm Co (II) | 9.9 |
| 4-MBA (15 mM) + 3 ppm Co (II) | 12.0 |
| 4-MBA (15 mM) + 5 ppm Co (II) | 11.5 |
| 4-MBA (15 mM) + 7 ppm Co (II) | 10.6 |
| 4-MBA (15 mM) + 10 ppm Co (II) | 11.4 |
| *pH = 8; 25° C.; 30 min. wash; 2.1 g/l detergent base | |
| Bleaching Tea Stains by Air and 4-Ethylbenzaldehyde With Cobalt Acetate (3 ppm/Cobalt) | |
| 4-MBA (1 mM) + Co $(OAc)_2$ | −0.3 |
| 4-MBA (3 mM) + Co $(OAc)_2$ | 0.9 |
| 4-MBA (5 mM) + Co $(OAc)_2$ | 14.3 |
| 4-MBA (10 mM) + Co $(OAc)_2$ | 14.7 |
| 4-MBA (15 mM) + Co $(OAc)_2$ | 15.7 |
| *pH = 8; 25° C.; 30 min. wash; 2.1 g/l detergent base | |

EXAMPLE 8

This Example evaluates the effect of magnesium, manganese and iron in the catalysis of 4-ethylbenzaldehyde bleaching. Table VIII establishes that magnesium, which is not a transition metal, is incapable of catalyzing the peroxidation. Manganese is slightly more effective but iron is optimum.

TABLE VIII

Bleaching Tea Stains by Air and 4-Ethylbenzaldehyde With Various Transition Metal Salts

| BLEACH SYSTEM | $\Delta\Delta R_{ave}$ |
|---|---|
| 4-EBA (15 mM) + 1 ppm Mg (II) | 0.5 |
| 4-EBA (15 mM) + 3 ppm Mg (II) | 0.9 |
| 4-EBA (15 mM) + 5 ppm Mg (II) | 0.3 |
| 4-EBA (15 mM) + 7 ppm Mg (II) | 0.4 |
| 4-EBA (15 mM) + 10 ppm Mg (II) | 0.2 |
| 4-EBA (15 mM) + 1 ppm Mn (II) | 0.6 |
| 4-EBA (15 mM) + 3 ppm Mn (II) | 0.8 |
| 4-EBA (15 mM) + 5 ppm Mn (II) | 0.9 |
| 4-EBA (15 mM) + 7 ppm Mn (II) | 1.2 |
| 4-EBA (15 mM) + 10 ppm Mn (II) | 1.3 |
| 4-EBA (15 mM) + 1 ppm Fe (II) | 2.0 |
| 4-EBA (15 mM) + 3 ppm Fe (II) | 7.2 |
| 4-EBA (15 mM) + 5 ppm Fe (II) | 8.1 |
| 4-EBA (15 mM) + 7 ppm Fe (II) | 8.3 |
| 4-EBA (15 mM) + 10 ppm Fe (II) | 7.5 |

*pH = 8; 25° C.; 30 min. wash; 2.1 g/l detergent base

EXAMPLE 9

TABLE IX

Bleaching Tea Stains By Air and 4-Ethylbenzaldedyde with Iron Acetate (5 ppm Fe)

| BLEACH SYSTEM | $\Delta\Delta R_{ave}$ |
|---|---|
| TAED (2%)/Perborate (8%) | 1.2 |
| 4-EBA (0.25 mM) + Fe $(OAc)_2$ | −1.0 |
| 4-EBA (0.5 mM) + Fe $(OAc)_2$ | −1.1 |
| 4-EBA (1 mM) + Fe $(OAc)_2$ | −0.9 |
| 4-EBA (1.5 mM) + Fe $(OAc)_2$ | 0.4 |
| 4-EBA (3 mM) + Fe $(OAc)_2$ | 3.2 |
| 4-EBA (5 mM) + Fe $(OAc)_2$ | 4.7 |
| 4-EBA (10 mM) + Fe $(OAc)_2$ | 8.8 |
| 4-EBA (15 mM) + Fe $(OAc)_2$ | 8.0 |

*pH = 8; 25° C., 30 minutes wash; 2.1 g/l detergent base

TABLE X

Bleaching Tea Stains by Air and 4-Ethylbenzaldehyde with Iron Acetate (3 ppm Fe)

| BLEACH SYSTEM | $\Delta\Delta R_{ave}$ |
|---|---|
| TAED (2%)/Perborate (8%) | 1.2 |
| 4-EBA (1 mM) + Fe $(OAc)_2$ | −0.2 |
| 4-EBA (1.5 mM) + Fe $(OAc)_2$ | −1.6 |
| 4-EBA (2 mM) + Fe $(OAc)_2$ | 2.1 |
| 4-EBA (3 mM) + Fe $(OAc)_2$ | 3.4 |
| 4-EBA (5 mM) + Fe $(OAc)_2$ | 5.0 |
| 4-EBA (10 mM) + Fe $(OAc)_2$ | 8.8 |
| 4-EBA (15 mM) + Fe $(OAc)_2$ | 8.3 |

*pH = 8; 25° C., 30 minutes wash; 2.1 g/l detergent base

Tables IX and X reveal that iron acetate both at 3 and 5 ppm active iron, when combined with 4-ethylbenzaldehyde produces a highly effective bleaching system.

EXAMPLE 10

The following formulations are typical of laundry cleaning compositions according to the present invention.

| | FORMULATION (% BY WEIGHT) | | | | |
|---|---|---|---|---|---|
| INGREDIENT | A | B | C | D | E |
| 4-Ethylbenzaldehyde | 10.4 | 10.4 | 10.4 | 10.4 | 10.4 |
| Iron (II) Acetate | 3 ppm | — | — | — | — |
| Iron (II) Sulfate | — | 3 ppm | — | — | — |
| Iron (III) Chloride | — | — | 8 ppm | — | — |
| Cobalt (II) Acetate | — | — | — | 5 ppm | — |
| Cobalt (III) Acetyl-acetonate | — | — | — | — | 5 ppm |
| Linear Alkylbenzene Sulphonate | 22 | 22 | 22 | 22 | 22 |
| Sodium Carbonate | 15 | 15 | 15 | 15 | 15 |
| Sodium Tripoly-phosphate | 13.3 | 13.3 | 13.3 | 13.3 | 13.3 |
| Sodium Silicate | 7.3 | 7.3 | 7.3 | 7.3 | 7.3 |
| Water | 6.0 | 6.0 | 6.0 | 6.0 | 6.0 |
| Optical Brightener | 0.22 | 0.22 | 0.22 | 0.22 | 0.22 |
| Sodium Carboxymethylcellulose | 0.35 | 0.35 | 0.35 | 0.35 | 0.35 |
| Colorant | 0.015 | 0.015 | 0.015 | 0.015 | 0.015 |
| Protease | 0.64 | 0.64 | 0.64 | 0.64 | 0.64 |
| Lipase | 0.14 | 0.14 | 0.14 | 0.14 | 0.14 |
| Sodium Sulphate | balance | balance | balance | balance | balance |

The foregoing description and examples illustrate selected embodiments of the present invention. In light thereof variations and modifications will be suggested to one skilled in the art, all of which are within the spirit and purview of this invention.

What is claimed is:

1. A bleaching composition comprising:

(i) an effective amount for stain removal of a $C_7$–$C_{20}$ aromatic aldehyde;

(ii) air as a primary source of oxygen atoms to combine with the aldehyde; and (iii) an effective amount to activate the aldehyde of an uncomplexed transition metal salt wherein said bleaching composition is delivered in a form selected from the group consisting of a powder, sheet, pouch, tablet, aqueous liquid, aerosol, gel, cream and granular form.

2. The composition according to claim 1 wherein the transition metal is selected from the group consisting of iron, manganese, cobalt, molybdenum, tungsten, titanium, vanadium and mixtures thereof.

3. The composition according to claim 1 wherein the aromatic aldehyde is a liquid and contains from 7 to 10 carbon atoms.

4. The composition according to claim 1 wherein the aromatic aldehyde is selected from the group consisting of 2-methylbenzaldehyde, 3-methylbenzaldehyde, 4-methylbenzaldehyde, 2-chlorobenzaldehyde, 3-trifluoromethylbenzaldehyde, 3,4-dimethylbenzaldehyde, 3,5-dimethylbenzaldehyde, 2,4-dimethylbenzaldehyde, 2,5-dimethylbenzaldehyde, 2-trifluoromethylbenzaldehyde, 2-ethylbenzaldehyde, 3-ethylbenzaldehyde, 4-ethylbenzaldehyde, 2,4,6-trimethylbenzaldehyde and mixtures thereof.

5. The composition according to claim 1 further comprising from about 1 to about 80% of a detergent builder.

6. The composition according to claim 1 further comprising from about 0.5 to about 50% of a surfactant.

7. The composition according to claim 1 further comprising an effective amount for cleaning of an enzyme selected from the group consisting of proteases, cellulases, lipases, amylases, peroxidases and mixtures thereof.

8. The composition according to claim 1 wherein the aromatic aldehyde is present in an amount from about 0.1% to about 50% and a transition metal salt present in an amount from about 0.1 ppm to about 5% by weight.

9. A method for bleaching a stained substrate, the method comprising contacting the stained substrate in an aqueous medium in air with a $C_7$–$C_{20}$ aromatic aldehyde, a surfactant in an effective amount to clean the substrate and an uncomplexed transition metal salt.

10. The method according to claim 9 wherein the aromatic aldehyde and transition metal salt are present in a weight ratio of about $1\times10^9$:1 to about 1:2.

11. The method according to claim 9 wherein the substrate is selected from the group consisting of fabrics, household fixtures and kitchenware.

12. The method according to claim 9 wherein the substrate is a denture.

13. A method for bleaching a stained substrate, the method comprising contacting the stained substrate in air in an aqueous medium with a $C_7$–$C_{20}$ aromatic aldehyde and an uncomplexed transition metal salt.

* * * * *